(12) United States Patent
Rupp et al.

(10) Patent No.: US 6,733,443 B2
(45) Date of Patent: May 11, 2004

(54) RETRACTION PLATE FOR SOFT-TISSUE PARTS

(75) Inventors: Stephan Rupp, Davos-Dorf (CH); Markus Hehli, Frauenkirch (CH)

(73) Assignee: Synthes (USA), Paoli, PA (US)

( * ) Notice: Subject to any disclaimer, the term of this patent is extended or adjusted under 35 U.S.C. 154(b) by 31 days.

(21) Appl. No.: 09/859,639

(22) Filed: May 18, 2001

(65) Prior Publication Data

US 2002/0007112 A1 Jan. 17, 2002

Related U.S. Application Data

(63) Continuation of application No. PCT/CH98/00499, filed on Nov. 20, 1998.

(51) Int. Cl.$^7$ .................................................. A61B 1/32
(52) U.S. Cl. ...................... 600/213; 600/210; 600/235; 600/37
(58) Field of Search .................. 600/37, 201, 210, 600/213, 228, 235, 206, 227; 606/232

(56) References Cited

U.S. PATENT DOCUMENTS

| | | | | |
|---|---|---|---|---|
| 5,337,736 A | * | 8/1994 | Reddy | 600/37 |
| 5,520,608 A | | 5/1996 | Cabrera et al. | 600/201 |
| 5,681,311 A | | 10/1997 | Foley et al. | 606/61 |
| 5,716,326 A | | 2/1998 | Dannan | 600/204 |
| 5,803,903 A | | 9/1998 | Athas et al. | 600/231 |
| 5,810,721 A | * | 9/1998 | Mueller et al. | 600/206 |
| 5,894,843 A | * | 4/1999 | Benetti et al. | 128/898 |
| 5,976,069 A | * | 11/1999 | Navia et al. | 600/37 |
| 6,015,382 A | * | 1/2000 | Zwart et al. | 600/207 |
| 6,033,362 A | | 3/2000 | Cohn | 600/213 |
| 6,090,042 A | * | 7/2000 | Rullo et al. | 600/210 |
| 6,251,065 B1 | * | 6/2001 | Kochamba et al. | 600/37 |
| 6,319,193 B1 | * | 11/2001 | Arai et al. | 600/37 |
| 6,346,077 B1 | * | 2/2002 | Taylor et al. | 600/204 |

FOREIGN PATENT DOCUMENTS

| | | |
|---|---|---|
| DE | 43 43 117 A1 | 6/1995 |
| DE | 295 07 637 | 8/1995 |
| WO | WO 98/48704 | 11/1998 |

* cited by examiner

*Primary Examiner*—Jeffrey A. Smith
(74) *Attorney, Agent, or Firm*—Jones Day

(57) ABSTRACT

The present invention relates to a retraction plate for displacing soft tissue. The plate includes a window located in between first and second end parts. Each of the end parts has connecting elements for removably securing an elongate element. Coupling of elongate elements to the connecting elements allows lifting of the plate to retract soft tissue, thereby creating a cavity between the soft-tissue mantle and bone to perform a surgical procedure. The retraction plate provides access to a fracture and allows fracture fixation using a minimally invasive surgical technique.

57 Claims, 3 Drawing Sheets

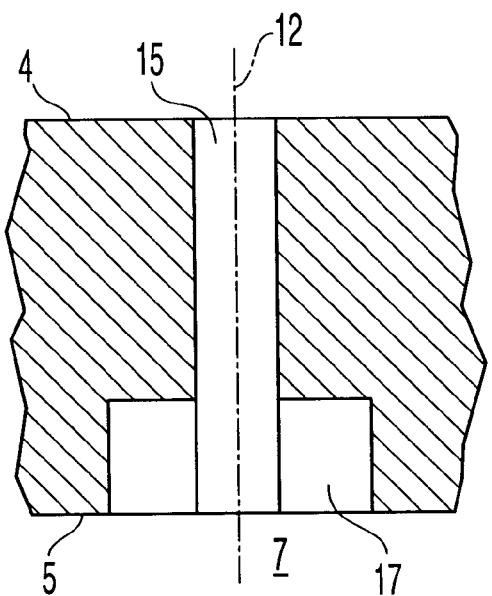
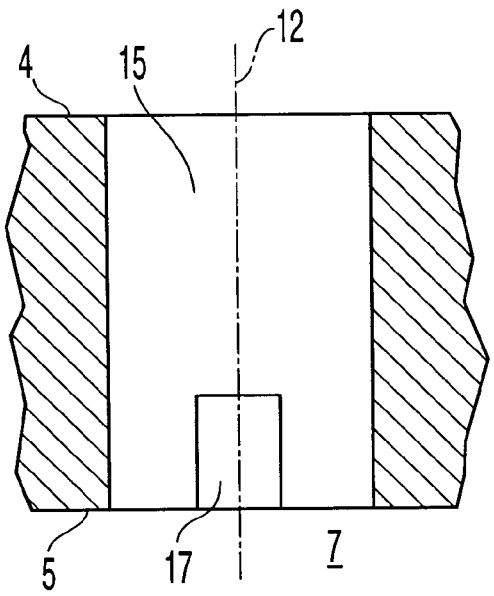
Fig. 8  Fig. 9
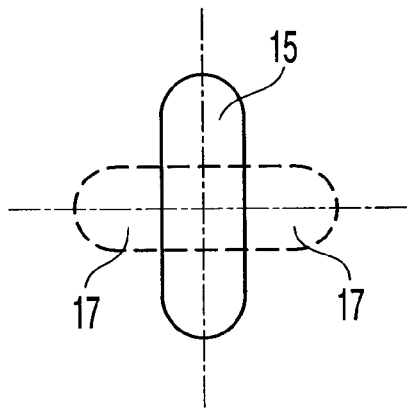
Fig. 10
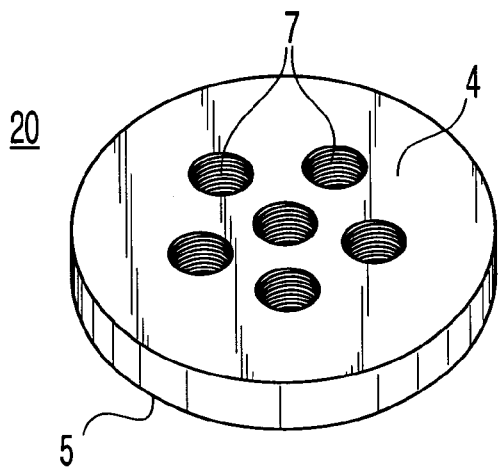
Fig. 11

# RETRACTION PLATE FOR SOFT-TISSUE PARTS

CROSS-REFERENCE TO RELATED APPLICATIONS

This application is a continuation of the U.S. national stage designation of copending International Patent Application PCT/CH98/00499, filed Nov. 20, 1998, the entire content of which is expressly incorporated herein by reference thereto.

FIELD OF THE INVENTION

The present invention concerns a surgical retractor, and in particular to a device for creating an artificial cavity by distracting soft-tissue.

BACKGROUND OF THE INVENTION

Surgical retractors for positioning tissue at a surgical site are known in the related art as an aid in performing surgical procedures. One such device is known from U.S. Pat. No. 6,033,362 to Cohn ("Cohn"). This known surgical retractor is used for minimally invasive direct coronary bypass procedures to arrest movement of the grafting site while the heart continues pumping. The surgical retractor disclosed by Cohn has a single handle for detachably connecting the retractor to a manipulating instrument. The single handle, however, limits the ease and ability of the plate to be quickly and reliable positioned at surgical sites located in the torso, arms, or legs. Thus, there exists a need for an improved retraction device.

SUMMARY OF THE INVENTION

The present invention relates to a tissue retraction plate for displacement of soft tissue. The plate has upper and lower surfaces and a plurality of connecting elements. Each connecting element is configured and dimensioned to removably secure an elongate member. Coupling of the elongate members to the connecting elements allows lifting of the plate to retract soft tissue thereby creating a cavity to perform a surgical procedure.

In one embodiment, the plate has a disk shape. In another embodiment, the plate has a longitudinal axis and comprises first and second ends, a middle portion therebetween, and a window on the middle portion and extending from the upper surface through the lower surface. The window forms an opening for performing a surgical procedure. The connecting elements can be positioned on the first and second ends. In one embodiment, the window comprises about 60% to about 75% of the middle portion of the plate. In another embodiment, the window comprises about 35% to about 57% of the upper side of the plate. In yet another embodiment, a ratio of a first area defined by the first and second ends to a second area defined by the middle portion ranges from about 0.40 to about 0.60. The connecting elements can be arranged symmetrically about the longitudinal axis of the plate, and can be divided into a first set located on the first end of the plate, and a second set located on the second end of the plate. The first and second sets can be substantially identical.

A number of mechanisms can be used to couple the elongate members to the connecting elements. In one embodiment, each of the connecting elements comprises a bore each having a central axis, an inner diameter, and a threaded inner surface, with the central axis of the bore substantially perpendicular to the longitudinal axis of the plate. The bore can be cylindrical, or taper from the upper surface to the lower surface. In another embodiment, at least one of the connecting elements comprises a bore extending from the upper surface to the lower surface of the plate, and has a slot on the lower surface intersecting the bore and operatively configured to slidably receive a rod having a T-end.

The present invention also relates to a retraction device for retracting soft tissue. The device includes the above-described retraction plate and at least two rods. Each rod has an end configured and dimensioned to be detachably secured to one of the connecting elements. Coupling of the rods to the connecting elements allows lifting of the plate to retract soft tissue, thereby creating a cavity to perform a surgical procedure. As previously noted, the plate can have a longitudinal axis and includes first and second ends and a window located there between and extending from the upper surface through the lower surface. The window forms an opening for performing the surgical procedure. Connecting elements can be located on the first and second ends. In one embodiment, each connecting element comprises a bore having an inner thread and the ends of each rod are threaded and configured to mate with the inner thread. In another embodiment, at least one of the connecting elements comprises a cylindrical bore extending from the upper surface to the lower surface of the plate. The lower surface of the plate has a slot intersecting the bore and operatively configured to slidably receive a rod having a T-end.

The present invention also relates to a method for retracting soft tissue. An incision is made, and fascia near the incision are separated to create an opening. The above described retraction plate is inserted through the incision and into the opening. Elongate members are then coupled to plate connecting elements. The coupled elongate members are then pulled to retract soft tissue, for accessing a surgical site through the plate window to perform a surgical procedure. Additionally, the plate may be bent, or a cavity may be created with an inflatable member to facilitate soft tissue retraction according to the method of the present invention.

BRIEF DESCRIPTION OF THE DRAWINGS

Preferred features of the present invention are disclosed in the accompanying drawings, wherein similar reference characters denote similar elements throughout the several views, and wherein:

FIG. 8 is a cross sectional view through line 8—8 of FIG. 1, showing an embodiment of a connecting element for releasably securing the manipulating rod of FIG. 7.

FIG. 9 is a cross sectional view through line 9—9 of FIG. 1, showing the connecting element of FIG. 8.

FIG. 10 is plan view of the connecting element of FIGS. 8 and 9.

FIG. 11 is a perspective view of an embodiment of a disk-shaped retraction plate having six illustrative connecting elements for releasably securing a manipulating rod.

DETAILED DESCRIPTION OF THE PREFERRED EMBODIMENTS

Figure 1:
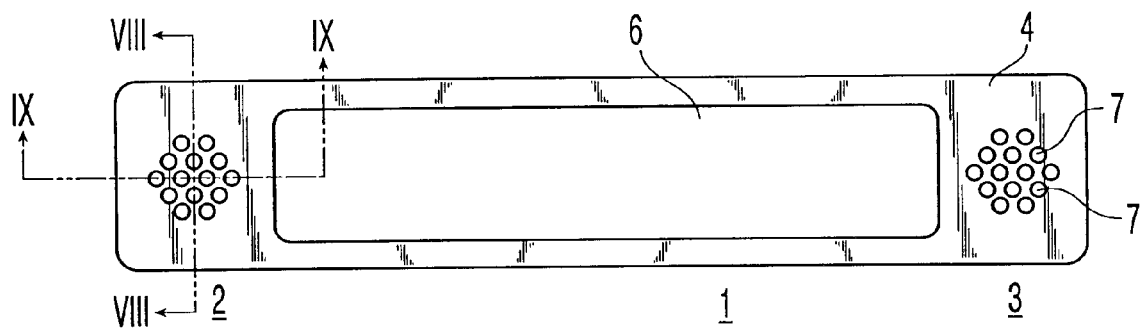
FIG. 1 is a plan view of one embodiment of a retraction plate according to the present invention.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto.

Figure 2:
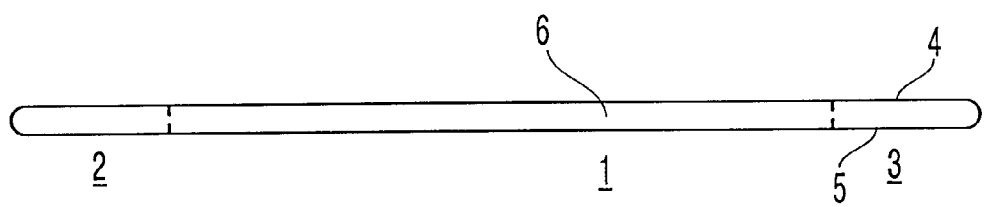
FIG. 2 is a elevation view of the retraction plate of FIG. 1.

Referring to FIGS. 1 and 2, in an illustrative embodiment the retraction plate has a middle part 1, two end parts 2, 3 separated from one another by the middle part 1, an upper side 4 and a lower side 5. The middle part 1 has an opening 6 in the form of a window which extends from the upper side 4 through the lower side 5. The window permits a surgeon to work from above and through the opening. For example, a bone plate can be attached directly to a bone through the window, or a fixating element may be secured to a bone through the window. Additionally, the sides of the window (i.e., the window frame) may be operably configured and dimensioned to be pliable, readily bent, and adapted by the surgeon manually or with an instrument to meet a specific clinical need. Similarly, the retraction plate can be manufactured in various lengths and shapes. For example, and as described below, the retraction plate may have a disk shape.

Referring to FIG. 1, the window area 6 may account for about 60% to about 75% of the middle part 1, and preferably may account for about 64% to about 72%. The window area 6 may further comprise about 35% to about 57% of the upper surface, and preferably may comprise a range between about 41% to about 50% of the upper surface. Alternatively, where F1 represents the area of the upper surface comprising the middle part 1, and F2 represents the upper surface area comprising the first end part 2, and F3 represents the upper surface area of the second end part 3; the ratio of (F2+F3)/(F1) ranges from about 0.40 to about 0.60, and preferably ranges from about 0.45 to about 0.55.

Figure 3:
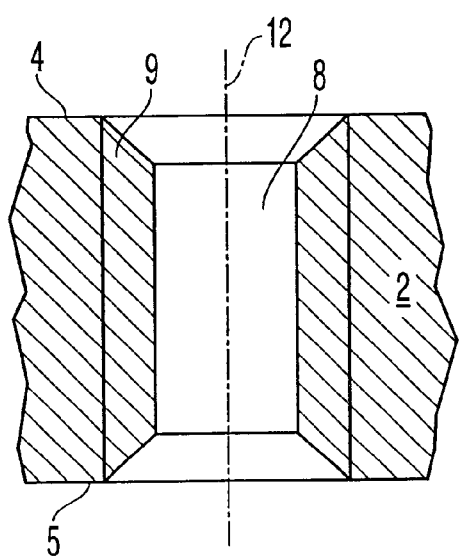
FIG. 3 is a cross sectional view through one embodiment of a connecting element for releasably securing a manipulating rod to the plate.
Figure 4:
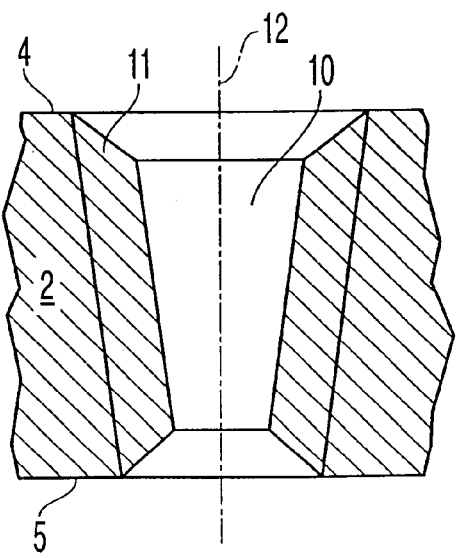
FIG. 4 is a cross sectional view through another embodiment of a connecting element for releasably securing a manipulating rod to the plate.
Figure 7:
FIG. 7 is a longitudinal sectional view of another embodiment of a manipulating rod with a T-end, operably configured to be securable to the connecting element of FIGS. 8–10.`
Figure 5:
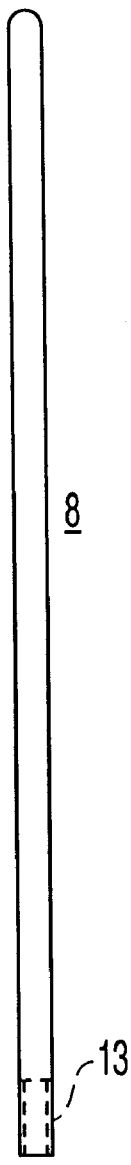
FIG. 5 is an elevational view of an embodiment of a manipulating rod operably configured to be releasably secured to the connecting element of FIG. 3.
Figure 6:
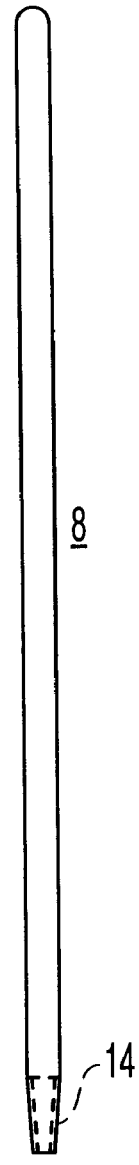
FIG. 6 is an elevational view of another embodiment of a manipulation rod operably configured to be releasably secured to the connecting element of FIG. 4.

Referring to FIGS. 1–4, the end parts 2, 3 of the retraction plate have a plurality of symmetrically arranged connecting elements 7, for releasably securing a free end of a manipulating rod 8 or elongate member, shown in FIGS. 5–7. One skilled in the art would readily appreciate that there are many methods and systems that can be used to releasably secure manipulating rods to the plate, such that at least one manipulating rod becomes coupled to the first and second end parts 2, 3, respectively.

In one embodiment, a connecting element 7 illustrated in FIG. 3 and comprising a cylindrical bore with an inside thread 9 and whose central axis 12 is perpendicular to the retraction plate may be used to releasably secure a manipulating rod 8, illustratively shown in FIG. 5, having an outer thread 13 on a free end so that it may be screwed into the bore. In this embodiment the central axis 12 of bore is perpendicular to the retraction plate.

In another embodiment, a connecting element 7 illustrated in FIG. 4 and comprising a conical-shaped bore 10 having an inside thread 11, and where the conical bore 10 tapers from the upper side 4 toward the lower side 5 may be used to releasably secure a manipulating rod 8, illustratively shown in FIG. 6 with a conical outside thread 14 on a free end so that it can be screwed into the bore 10. In this embodiment the central axis 12 of bore 10 is perpendicular to the retraction plate.

Other thread embodiments may also be used to secure a manipulating rod. For example, a rod with a tapered free end (e.g., conically shaped) may be operably configured to be fully secured within a bore by a one-half revolution turn or a one-revolution turn of the rod. By contrast, another rod with a uniform diameter may be operably configured and dimensioned to be fully secured to a bore by multiple revolutions of the rod. Similarly, the plate connecting element 7 are preferably designed so that the manipulating rods 8 may be connected in a vertical direction relative to the retraction plate. Other embodiments of the connecting elements 7, however, may be designed wherein the manipulating rods 8 are attached to the plate at an angle α, which is measured from an axis perpendicular to the retraction plate. In one embodiment, the angle a ranges from about 25° to about 50°, and preferably ranges from about 35° to about 45°.

In another embodiment, a connecting element 7 illustrated in FIGS. 7–10 and comprising an elongated hole 15 extends from the upper surface to the lower surface of the plate. A slot 17 disposed within the lower surface 5 of the plate and which is configured to intersect the elongated hole 15 comprises a catch mechanism for a manipulating rod having a T-end or cross bar 16 at one free end. The manipulating rod 8 having a T-end 16 is operably designed and configured to be slidably inserted into elongated hole 15 and to be pushed through the elongated hole from the upper surface past the lower surface of the plate, where upon suitable rotation of the rod would allow the T-end to be retracted into slot 17. Preferably the T-end would be rotated about 90° from the longitudinal axis of elongated hole 15 to fit into slot 17. Manipulating rods 8 would thereby be secured to the retraction plate under tensile forces but would disengage under compressive forces. Manipulating rods 8 coupled to the plate in this manner may still move in a conical pattern of a few degrees. Preferably, the angle of movement is within 40° of the central axis 12 of connecting element 7.

One skilled in the art would readily appreciate that the connecting elements disclosed in the foregoing paragraphs do not comprise an exclusive collection of embodiments for releasably securing a manipulating rod to the retraction plate. For example, a bayonet closure or another flexible connecting element may be used.

Referring to FIG. 11, retraction disk 20 shows another embodiment of the present invention. The retraction disk may also be used to displace soft tissue parts in surgical procedures, and has an upper 4 and lower 5 sides, and a plurality of symmetrically arranged connecting elements 7 in the area of its upper side 4, which are substantially identical to the connecting elements previously described. Thus, retraction disk 20 corresponds functionally to the end parts 2, 3 of the retraction plate according to FIG. 1.

The method of the present invention makes it possible to lift soft tissue parts away from bone during surgery, and to create an artificial cavity so that the surgical procedure may be performed more easily and reliably. More specifically, the device and method of the present invention relate to creating artificial cavities for performing surgery in parts of the body where natural cavities are absent, such as in the extremities.

The procedure for creating the cavity typically involves making a suitable incision near the surgical site and separating two fascia to form an opening. A suitable device such as a balloon-tipped catheter may then be used to create a cavity between the fascia to facilitate placement and assembly of the retraction device. The cavity forming device would then be removed from the artificial cavity. A retraction plate of the present invention would be inserted through the main incision into the opening or artificial cavity. Manipulating rods are then releasably secured to the retraction plate via puncture incisions, and once secured the manipulating rods and plate are pulled away from the surgical site thereby creating a cavity between the retraction plate and bone. The rods can be suspended on an external suspension to lift the soft tissue. A forceps operably configured to releasably lock into the retraction plate may also be used to guide the plate into a desired position, and to prevent the retraction plate from twisting as the manipulating rods are secured.

One skilled in the art would readily appreciate the advantages of the present invention. For example, the present invention provides free access to a fracture, and facilitates the use of optical equipment to monitor surgical procedures such as repositioning the fracture, positioning a fixating device relative to the fracture, and securing the fixating device. In addition, the position of the retraction plate can be monitored with an optical system, allowing the manipulating rods to be releasably secured to the plate connecting elements through a puncture incision or another minimally invasive technique. To facilitate coupling of a manipulating rod with the connecting elements of a plate deployed under soft tissue during a blind search (although supported with an optical system), a plurality of connecting elements are located on the retraction plate. The present invention thereby limits disruption of circulation, which is very important to the healing process and reduces the potential for incorrectly securing bone plates and fixation elements. This results in reduced trauma and risk of complications arising from the surgical procedure. Accordingly, patients may also enjoy cosmetic benefits and potentially shorter periods of hospitalization.

While various descriptions of the present invention are described above, it should be understood that the various features can be used singly or in any combination thereof. Therefore, this invention is not to be limited to only the specifically preferred embodiments depicted herein. For instance, the foregoing embodiments are described on the basis of the retraction plate, but a similar description also applies to the retraction disk, which corresponds functionally to the two end parts of the retraction plate. Depending on the application, multiple retraction disks may be used in place of, or cooperatively, with a retraction plate. Similarly, other suitable plate connecting elements and manipulating rod configurations may be used.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A tissue retraction device for displacement of soft tissue comprising a substantially rigid plate having upper and lower surfaces adapted to contact soft tissue and a plurality of connecting elements, each connecting element configured and dimensioned to removably secure an elongate member, wherein the connecting elements form one or more clusters to facilitate coupling of the elongate member with one of the connecting elements during a blind search through soft tissue, and the coupling of the elongate member to one of the connecting elements allows lifting of the plate to retract soft tissue, wherein the plate has substantially constant stiffness during a medical procedure.

2. The device of claim 1, wherein the plate has a longitudinal axis and comprises first and second ends, a middle portion therebetween, and a window located on the middle portion and extending from the upper surface through the lower surface, the window forming an opening for performing a surgical procedure.

3. The device of claim 2, wherein the plurality of connecting elements are located on the first and second ends.

4. The device of claim 3, wherein the window comprises about 60% to about 75% of the middle portion of the plate.

5. The device of claim 3, wherein the window comprises about 35% to about 57% of the upper side of the plate.

6. The device of claim 3, wherein a ratio of a first area defined by the first and second ends to a second area defined by the middle portion ranges from about 0.40 to about 0.60.

7. The device of claim 3, wherein the connecting elements are arranged symmetrically about the longitudinal axis of the plate.

8. The device of claim 7, wherein the plurality of connecting elements comprises a first set of connecting elements located on the first end of the plate, and a second set of connecting elements located on the second end of the plate.

9. The device of claim 8, wherein the first and second sets are substantially identical.

10. The device of claim 3, wherein each of the connecting elements comprises a bore each having a central axis, an inner diameter, and a threaded inner surface, with the central axis of the bore substantially perpendicular to the longitudinal axis of the plate.

11. The device of claim 10, wherein each bore is cylindrical.

12. The device of claim 10, wherein the inner diameter of each bore tapers from the upper surface to the lower surface.

13. The device of claim 3, wherein at least one of the connecting elements comprises a cylindrical bore extending from the upper surface to the lower surface of the plate, and wherein the lower surface has a slot intersecting the bore and operatively configured to slidably receive a rod having a T-end.

14. The device of claim 1, wherein the plate has a disk shape.

15. The device of claim 1, wherein the plurality of connecting elements are symmetrically arranged on the plate.

16. The device of claim 1, wherein the plate has a substantially homogeneous composition.

17. The device of claim 1, wherein the plate is of one piece construction.

18. The device of claim 1, wherein the plate is malleable.

19. The device of claim 18, wherein the plate is capable of being shaped by hand.

20. The device of claim 1, wherein the plate is substantially polygonal.

21. The device of claim 1, wherein the plate is substantially free of projections.

22. The device of claim 1, wherein the plate has a predetermined thickness which cannot substantially change over time.

23. The device of claim 1, wherein the plate comprises a plurality of sides and one or more of the connecting elements are located on the side of the plate comprising a tissue retraction surface.

24. The device of claim 1, wherein one or more connecting elements adjoin the upper surface.

25. The device of claim 1, wherein each cluster has three or more collinear connecting elements.

26. The device of claim 1, wherein each cluster has five or more connecting elements.

27. A retraction device for retracting soft tissue comprising:
the device of claim 1; and
at least two rods each having at least one end configured and dimensioned to be detachably secured to one of the connecting elements, wherein
coupling of the rods to the connecting elements allows lifting of the plate to retract soft tissue thereby creating a cavity to perform a surgical procedure.

28. The device of claim 27, wherein the plate has a longitudinal axis and comprises first and second ends and a window located therebetween and extending from the upper surface through the lower surface, the window forming an opening for performing the surgical procedure; and wherein the plurality of connecting elements are located on the first and second ends.

29. The device of claim 28, wherein each connecting element comprises a bore having an inner thread and the ends of each rod are threaded and configured to mate with the inner thread.

30. The device of claim 28, wherein at least one of the connecting elements comprises a cylindrical bore extending from the upper surface to the lower surface of the plate, and wherein the lower surface has a slot intersecting the bore and operatively configured to slidably receive a rod having a T-end.

31. A method for retracting soft tissue comprising:
making an incision;
separating fascia near the incision to create an opening;
inserting a plate having a window through the incision and into the opening;
coupling an at least one elongate member to the plate;
pulling the at least one elongate member to retract soft tissue while keeping the plate substantially unconnected to the soft tissue during the surgical procedure; and
accessing a surgical site through the plate window to perform a surgical procedure.

32. The method of claim 31, further comprising bending the plate.

33. The method of claim 31, further comprising creating a cavity between the fascia with an inflatable member.

34. A method for retracting soft tissue from bone comprising:
making an incision;
separating fascia near the incision to create an opening;
inserting a plate having a window through the incision and into the opening;
positioning the plate between soft tissue and bone;
coupling an at least one elongate member to the plate; and
pulling the at least one elongate member away from the bone to retract soft tissue, thereby creating a cavity between the plate and the bone; and
performing a surgical procedure through the plate window.

35. The method of claim 34, further comprising lifting the plate to retract soft tissue from bone by a minimally invasive surgical approach.

36. The method of claim 34, further comprising treating a fractured bone.

37. The method of claim 36, further comprising securing a bone plate to fractured bone.

38. A tissue retraction device for displacement of soft tissue comprising a plate having a substantially rigid tissue retraction surface and a plurality of connecting elements, each connecting element configured and dimensioned to removably secure an elongate member, wherein coupling of the elongate member to one of the connecting elements allows lifting of the plate to retract soft tissue, wherein the tissue retraction surface has substantially constant stiffness during a medical procedure.

39. The device of claim 38, wherein the plate has upper and lower surfaces, a longitudinal axis and comprises first and second ends, a middle portion therebetween, and a window located on the middle portion and extending from the upper surface through the lower surface, the window forming an opening for performing a surgical procedure.

40. The device of claim 39, wherein the plurality of connecting elements are located on the first and second ends.

41. The device of claim 40, wherein the window comprises about 60% to about 75% of the middle portion of the plate.

42. The device of claim 40, wherein the window comprises about 35% to about 57% of the upper side of the plate.

43. The device of claim 40, wherein a ratio of a first area defined by the first and second ends to a second area defined by the middle portion ranges from about 0.40 to about 0.60.

44. The device of claim 40, wherein the connecting elements are arranged symmetrically about the longitudinal axis of the plate.

45. The device of claim 44, wherein the plurality of connecting elements comprises a first set of connecting elements located on the first end of the plate, and a second set of connecting elements located on the second end of the plate.

46. The device of claim 45, wherein the first and second sets are substantially identical.

47. The device of claim 40, wherein each of the connecting elements comprises a bore each having a central axis, an inner diameter, and a threaded inner surface, with the central axis of the bore substantially perpendicular to the longitudinal axis of the plate.

48. The device of claim 47, wherein each bore is cylindrical.

49. The device of claim 47, wherein the inner diameter of each bore tapers from the upper surface to the lower surface.

50. The device of claim 40, wherein at least one of the connecting elements comprises a cylindrical bore extending from the upper surface to the lower surface of the plate, and wherein the lower surface has a slot intersecting the bore and operatively configured to slidably receive a rod having a T-end.

51. The device of claim 38, wherein the plate has a disk shape.

52. The device of claim 38, wherein the plurality of connecting elements are symmetrically arranged on the plate.

53. The device of claim 38, wherein the connecting elements abut the upper surface.

54. The device of claim 38, wherein the connecting elements form one or more clusters to facilitate coupling of the elongate member with one of the connecting elements during a blind search through soft tissue.

55. The device of claim 38, wherein the plate is substantially stiff.

56. A retraction device for retracting soft tissue comprising:

the device of claim 38; and at least two rods each having at least one end configured and dimensioned to be detachably secured to one of the connecting elements, wherein coupling of the rods to the connecting elements allows lifting of the plate to retract soft tissue thereby creating a cavity to perform a surgical procedure.

57. The device of claim 56, wherein the plate has a longitudinal axis and comprises first and second ends and a window located therebetween and extending from the upper surface through the lower surface, the window forming an opening for performing the surgical procedure; and wherein the plurality of connecting elements are located on the first and second ends.

* * * * *